(12) United States Patent　　　(10) Patent No.: US 11,833,295 B2
Greiner-Perth et al.　　　(45) Date of Patent: Dec. 5, 2023

(54) DISCHARGE HEAD FOR THE NASAL APPLICATION OF LIQUID FROM A PRESSURE RESERVOIR

(71) Applicant: Aptar Radolfzell GmbH, Radolfzell (DE)

(72) Inventors: Jürgen Greiner-Perth, Gottmadingen (DE); Felix Schmid, Öhningen (DE)

(73) Assignee: APTAR RADOLFZELL GMBH, Radolfzell (DE)

( * ) Notice: Subject to any disclaimer, the term of this patent is extended or adjusted under 35 U.S.C. 154(b) by 872 days.

(21) Appl. No.: 16/615,245

(22) PCT Filed: Apr. 13, 2018

(86) PCT No.: PCT/EP2018/059583
§ 371 (c)(1),
(2) Date: Nov. 20, 2019

(87) PCT Pub. No.: WO2018/224206
PCT Pub. Date: Dec. 13, 2018

(65) Prior Publication Data
US 2020/0171252 A1　　Jun. 4, 2020

(30) Foreign Application Priority Data
Jun. 8, 2017　(EP) .................................... 17175093

(51) Int. Cl.
*A61M 15/08*　　(2006.01)
*A61M 15/00*　　(2006.01)
(Continued)

(52) U.S. Cl.
CPC .......... *A61M 15/08* (2013.01); *A61M 15/009* (2013.01); *B05B 1/12* (2013.01); *B05B 1/3452* (2013.01)

(58) Field of Classification Search
CPC .. A61M 15/08; A61M 15/009; A61M 11/007; A61M 5/145; B05B 1/12;
(Continued)

(56) References Cited

U.S. PATENT DOCUMENTS 3,961,756 A * 6/1976 Martini ................. B05B 1/3452
　　　　　　　　　　　　　　　　　　　222/402.1
4,358,057 A　　11/1982 Burke
(Continued)

FOREIGN PATENT DOCUMENTS

CN　　　　1250854 A　　4/2000
CN　　　103764511 A　　4/2014
(Continued)

OTHER PUBLICATIONS

Machine Translation of EP1726538A1; accessed Apr. 13, 2023 (Year: 2023).*
(Continued)

*Primary Examiner* — Elliot S Ruddie
(74) *Attorney, Agent, or Firm* — FLYNN THIEL, P.C.

(57) ABSTRACT

A discharge head for the nasal application of pharmaceutical liquid from a pressure reservoir which has an outlet valve with a valve connector, to which force can be applied counter to a spring force in order to open the outlet valve. The discharge head has a nasal applicator which extends outward from an actuating surface and at the end of which a discharge opening is provided. The discharge opening is connected in a fluid-communicating manner to a hollow tube through an applicator channel of the nasal applicator, for connection to the pressure reservoir. The nasal applicator has an inner component connected integrally to the actuating surface and an outer component separate from the inner component and attached to the inner component in a surrounding manner. The discharge opening is provided in the
(Continued)

outer component, and the outer component and the inner component together bound the applicator channel.

22 Claims, 6 Drawing Sheets

(51) Int. Cl.
*B05B 1/12* (2006.01)
*B05B 1/34* (2006.01)

(58) Field of Classification Search
CPC .......... B05B 1/3452; B05B 1/00–3457; B65D 83/228; B65D 83/16–206; B65D 83/226; B65D 83/28; B65D 83/38; B65D 83/44
See application file for complete search history.

(56) References Cited

U.S. PATENT DOCUMENTS

| | | | |
|---|---|---|---|
| 4,706,888 A | 11/1987 | Dobbs | |
| 5,590,837 A | 1/1997 | Grogan | |
| 5,996,653 A | 12/1999 | Piccinino, Jr. | |
| 6,419,124 B1 | 7/2002 | Hennemann et al. | |
| D659,531 S | 5/2012 | Engel | |
| 9,085,409 B2 | 7/2015 | Brall | |
| 9,352,345 B2 | 5/2016 | Greiner-Perth | |
| 9,375,538 B2 | 6/2016 | Greiner-Perth et al. | |
| 9,381,531 B2 | 7/2016 | Auerbach et al. | |
| 10,076,602 B2 | 9/2018 | Gerber | |
| 2009/0050650 A1* | 2/2009 | Walters | B65D 83/205 222/402.11 |
| 2012/0222673 A1* | 9/2012 | Pardonge | B65D 83/753 128/200.23 |
| 2014/0217202 A1 | 8/2014 | Stein et al. | |
| 2015/0014368 A1* | 1/2015 | Greiner-Perth | B65D 83/201 222/402.13 |
| 2016/0325916 A1 | 11/2016 | Jasper et al. | |

FOREIGN PATENT DOCUMENTS

| | | | |
|---|---|---|---|
| CN | 103917302 A | 7/2014 | |
| CN | 203926928 U | 11/2014 | |
| CN | 104210743 A | 12/2014 | |
| CN | 105873625 A | 8/2016 | |
| DE | 69914204 T2 | 2/2005 | |
| DE | 102012200545 A1 | 7/2013 | |
| EP | 0040851 A1 | 12/1981 | |
| EP | 0729792 A2 | 9/1996 | |
| EP | 1726538 A1 * | 11/2006 | .......... B65D 83/205 |
| RU | 28026 Y1 | 3/2003 | |
| WO | 2009025697 A1 | 2/2009 | |
| WO | 2016156723 A1 | 10/2016 | |
| WO | 2017021878 A1 | 2/2017 | |

OTHER PUBLICATIONS

European Search Report issued in corresponding EP 17 17 5093 with English translation of categories of cited documents, dated Dec. 13, 2017 (8 pages).
European Search Report issued in corresponding EP 18 20 9877 with English translation of categories of cited documents, dated Jun. 26, 2019 (10 pages).
International Search Report issued in corresponding International Application No. PCT/EP2018/059583 with English translation date of mailing Sep. 13, 2018 (9 pages).
Written Opinion of International Searching Authority issued in corresponding International Application No. PCT/EP2018/059583 dated Sep. 13, 2018 (8 pages).
Russian Search Report issued in parallel Russian Patent Application No. 2019109788/14 dated Apr. 3, 2019 (2 pages).
Russian Office Action with English Translation issued in parallel Russian Patent Application No. 2019109788/14, dated Jun. 30, 2020 (24 pages).
Chinese Office Action issued in corresponding Chinese Application No. 202210280372.9 dated Aug. 16, 2023 (7 pages).

* cited by examiner

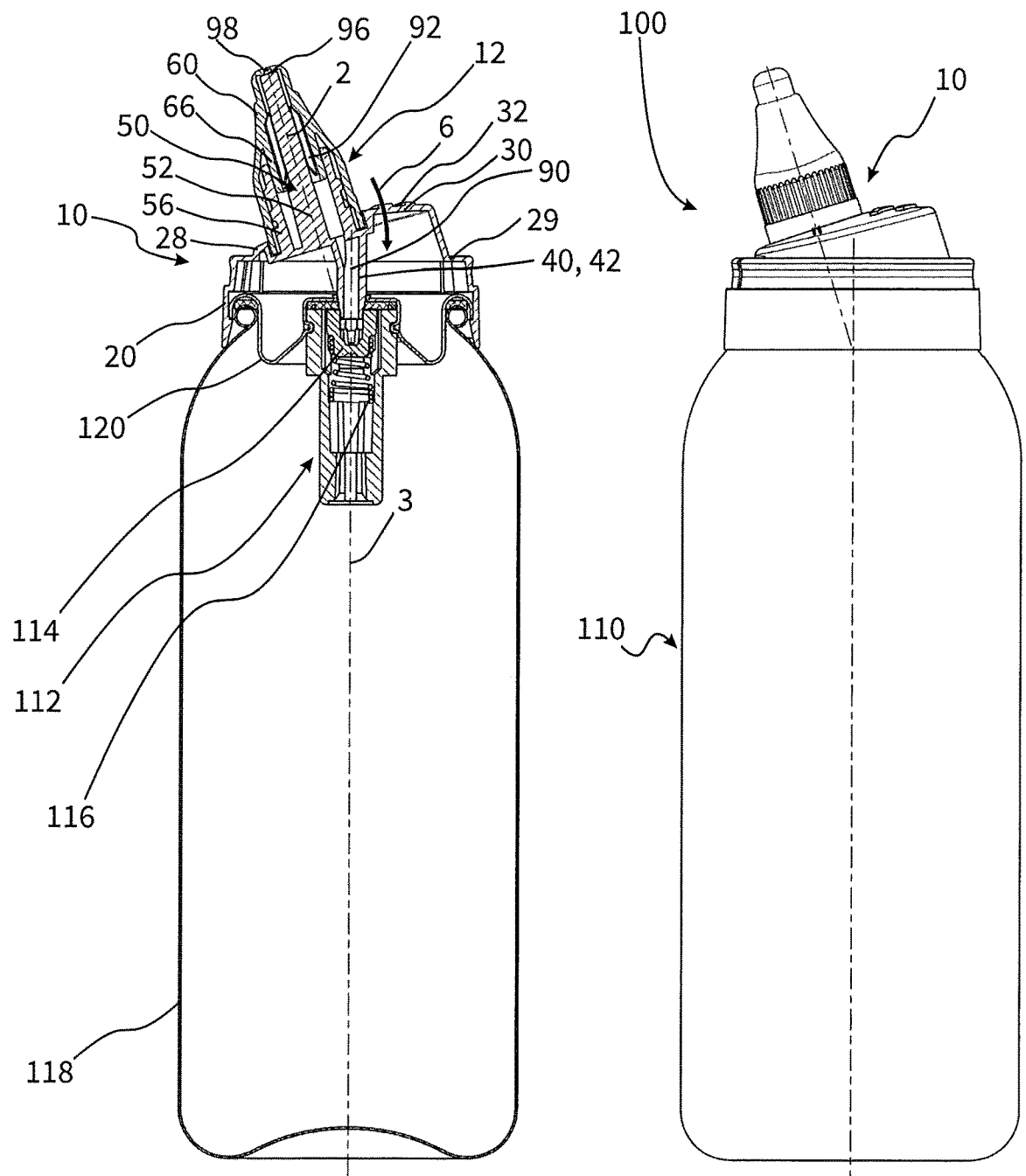
*Fig. 1A*
*Fig. 1B*
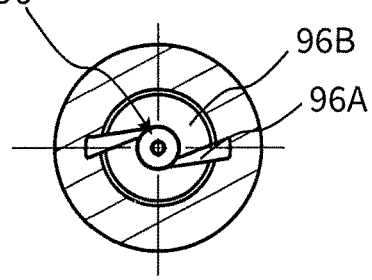
*Fig. 2*

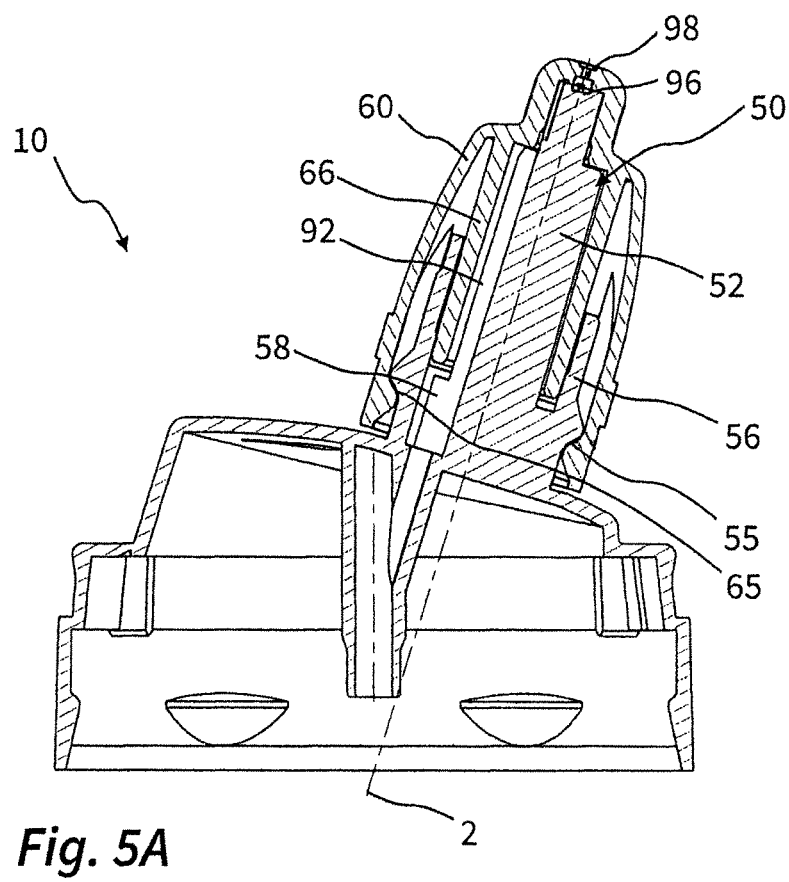
*Fig. 5A*
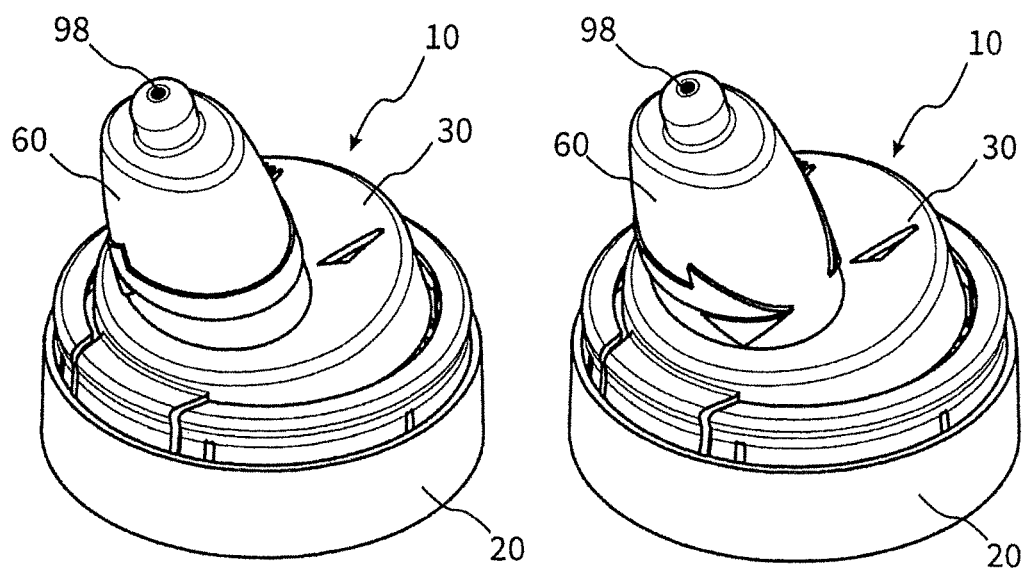
*Fig. 5B*   *Fig. 5C*

DISCHARGE HEAD FOR THE NASAL APPLICATION OF LIQUID FROM A PRESSURE RESERVOIR

FIELD OF USE AND PRIOR ART

The invention relates to a discharge head for the nasal application of pharmaceutical liquid from a pressure reservoir which has an outlet valve with a valve connector, to which force can be applied counter to a spring force in order to open the outlet valve. The invention furthermore also relates to a dispenser with such a discharge head.

Similar discharge heads and dispensers are known, for example, from DE 102012200545 A1. The discharge heads disclosed in this document have an outer housing which, firstly, contains the base for the connection to a pressure reservoir and, secondly, forms the outer shell of a nasal applicator together with a discharge opening. An inner component which, together with the outer shell, serves for fluid guidance of liquid to the discharge opening is pushed into the elongate nasal applicator.

A similar design is also known from the US design patent with the publication number U.S. D 659,531 S.

Discharge heads of the type in question are used for selling medicaments with a comparatively low sales price. The production of the discharge heads therefore has to be as reasonably priced as possible. The integral configuration, which is advantageous in this respect, of the outer housing together with the base and nasal applicator is readily suitable for achieving low costs. However, disadvantages are also provided. The liquid plastic within the scope of the injection molding operation is conventionally supplied in the region of the base. The discharge opening is therefore at a comparatively far distance from the supply point, which leads to sometimes unsatisfactory manufacturing accuracy at the discharge opening and at fluid directing surfaces upstream of the discharge opening. This is disadvantageous since the discharge behavior of the liquid may vary from dispenser to dispenser and no longer corresponds to the intended discharge behavior.

It is therefore the object of the invention to develop a dispenser of the type in question to the effect that high manufacturing accuracy is obtained in the region of the discharge opening without correspondingly increasing the complexity of the manufacturing.

According to a first aspect of the invention, a discharge head which, corresponding to discharge heads of the generic type, has a base, an actuating surface which is movable in relation thereto, and a nasal applicator. The base has a coupling device which is provided thereon and by means of which the discharge head is fastenable to the pressure reservoir.

The actuating surface is shiftable manually in relation to the base for the purpose of the actuation. A plunger in the manner of a hollow tube provided on the actuating surface is thereby shifted at the same time, and therefore the valve connector of the valve of the pressure reservoir can thereby be opened. The actuating surface is preferably provided with texturing, for example with a corrugation.

The nasal applicator extends outward from the actuating surface. The distal end thereof is provided with a discharge opening which is connected in a fluid-communicating manner to the hollow tube through an inner applicator channel of the nasal applicator.

According to the invention, the nasal applicator has an inner component which is connected integrally to the actuating surface. Furthermore, it has an outer component which is designed as a component separate from the inner component and is attached to the inner component in a manner surrounding the latter. The discharge opening is provided as an opening in the outer component. The applicator channel leading to the discharge opening is jointly bounded by the outer component and the inner component.

In a nasal applicator according to the invention, it is therefore provided that the discharge opening is formed by a component which is separated at least from the inner component and the actuating surface formed integrally therewith. The discharge opening is therefore part of an overall smaller component than in the configurations according to the prior art. This makes it possible to manufacture the discharge opening with greater precision and/or at higher cycle rates.

The discharge opening within the context of the invention should be understood as the end of the applicator channel, i.e. the transition point at which the pressurized liquid is dispensed into an outer environment under ambient pressure and, depending on the manner of exit through the discharge opening, is present there as a free jet or as a spray jet. The discharge opening preferably has a minimum cross-sectional area of less than 4 mm$^2$, in particular of less than 2 mm$^2$.

In addition to the advantage of better production capability, the design of the outer component as a component which is separate from the base is therefore also of advantage since the outer component can thereby be interchangeable, which is of advantage for hygiene reasons. In particular, the discharge opening at which liquid may remain after use can become rapidly contaminated. By exchanging the outer component, all or at least particularly at-risk regions are exchanged. The adaptation of the discharge head to a specific target group is also possible by means of the separate outer component. In particular, an adult-compatible or child-compatible configuration can be obtained by the selection of the appropriate outer component. It is possible here both for adaptations specific to a target group to already take place at the manufacturer and also for a plurality of outer components to be supplied at the same time to the final customer so that the final customer himself/herself can undertake the adaptation once or occasionally.

The nasal applicator is intentionally inserted into a nostril of the user. For this purpose, it is an elongate, slender applicator which preferably has a shape tapering to the distal end and the discharge opening. The nasal applicator preferably projects at least 20 mm from the level of the actuating surface. Its length which protrudes freely from the base or the actuating surface is preferably greater at least by a factor of 2, in particular preferably at least by a factor of 2.5, than the maximum diameter of the nasal applicator.

The base of the discharge head is the part which is intentionally coupled to the pressure reservoir. For this purpose, the coupling device is provided which is in particular snapped onto the pressure reservoir preferably via integrally formed latching edges. For this purpose, the base preferably has an annular structure with inwardly pointing latching lugs. In pressure reservoirs which may be used with a discharge head according to the invention, a crimp connection is provided between a cover and a casing, said crimp connection preferably being used for the snapping on of the latching lugs.

The inner component and the outer component together can form a vortex chamber mounted upstream of the discharge opening. A vortex chamber is understood here as meaning a chamber which is mounted upstream of the discharge opening and into which the liquid flows at least partially in a tangential direction or at least in a direction angled in relation to a radial direction.

Such a vortex chamber can have at least one directing surface for generating a swirl, said directing surface being inclined in relation to a radial direction. Said at least one directing surface can be provided on an inner side of the outer component, and therefore great manufacturing precision can be obtained during the injection molding, just like in the case of the discharge opening. The directing surface can be provided in particular as part of an inflow channel leading into the vortex chamber. A plurality of such inflow channels can be provided.

In principle, a configuration of the discharge head is possible, in which the outer component and the inner component are fixed in position with respect to each other in the mounted state.

However, the design according to the invention is particularly of advantage in a configuration in which the outer component is attached to the inner component in such a manner that, in the attached state, the outer component is movable relative to the inner component.

Accordingly, the inner component and the outer component permit the outer component to be moved in relation to the inner component. By this means, adaptation of the discharge head and in particular of the nasal applicator to different situations can be achieved, as will be explained further on.

The configuration according to the invention with an outer component placed onto the inner component permits such a configuration of a movable outer component in an advantageous design since the relative shifting can be undertaken by the user in a simple manner by force being applied to the outer component directly and manually in relation to the base.

The movement of the inner component and of the outer component can take place between two end positions which impede a continued movement or at least make said movement difficult. However, it can be expedient for a relative movement to be able to take place in one direction with increased force beyond the end position initially interrupting the relative movement, and therefore, with little effort, shifting between the end positions is possible and, with an application of force which is greater by comparison, the inner component and the outer component can be moved beyond said end position without destruction, and therefore the inner component and the outer component can thereby be separated from each other in order to exchange the outer component for a different one, for example for hygienic reasons.

The shiftability of the outer component and of the inner component in relation to each other can serve in particular for the purpose of changing the characteristics of the liquid discharge through the discharge opening.

For this purpose, the inner component and the outer component can be designed in such a manner that the applicator channel and/or the vortex chamber are/is variable geometrically by a relative shifting of the inner component and the outer component.

In particular, the inner component and the outer component can be designed in such a manner that the applicator channel is variable in respect of its clear cross section by a relative shifting. Depending on the region of the applicator channel in which the variation takes place, different effects can thereby be achieved.

If the applicator channel is widened or tapered far upstream of the discharge opening by means of a relative shifting, this leads to a throttling effect, by means of which in two different positions of the outer component relative to the inner component, at the same inflow pressure different liquid flows are dispensed through the discharge opening. It is therefore possible, for example, for an adult-compatible and child-compatible dosage to be set without said dosage having to take place by longer and shorter actuation.

If the applicator channel changes with respect to the clear width in the region of the vortex chamber ending said applicator channel, the characteristics of the liquid flowing out through the discharge opening can be influenced. In particular, it can thereby be achieved that, at the same inflow pressure, liquid having a differing extent of droplet formation or different droplet size is dispensed depending on the relative position.

This is achieved in particular by the fact that the action of a swirl-implementing geometry is increased or weakened owing to the fact that, depending on the relative position, a different portion of the liquid is conducted through swirl-implementing channels while the remaining portion is conducted past said swirl-implementing channels directly to the discharge opening.

For example, a design is possible in which a switch can be made between an unatomized liquid jet, also called jet, and an atomization. Additionally or alternatively, complete closing of the applicator channel may also be possible, and therefore a type of transport protection is provided.

The mentioned relative movability between the outer component and the inner component can be realized in various ways. It can thus be provided that the outer component is movable in a purely linear manner or in a purely rotational manner in relation to the inner component. A combination, particularly in which the outer component is movable in a combined linear and rotational manner in relation to the inner component, is also possible.

In the case of purely rotational shiftability, the applicator channel as a whole has a shape differing from rotational symmetry, and therefore the shape of the applicator channel can be influenced by rotation. Further possibilities for designing a purely rotational variant are also explained below.

In the case of a purely linear or combined linear movability, the discharge opening itself is also shifted axially in relation to the inner component by the shifting. This is suitable in particular in order, by means of this axial movement, to completely interrupt the applicator channel directly upstream of the vortex chamber or upstream of the discharge opening and/or to influence in the abovementioned manner which portion of liquid is intended to be swirled as it flows into a vortex chamber.

A depression can be provided in a transition region between the inner component and the actuating surface. A proximal edge of the outer component dips into said depression in at least one end position of the outer component in relation to the inner component.

The depression mentioned can be configured in the manner of a groove. A proximal end of the outer component facing the actuating surface and facing away from the discharge opening dips at least in phases into said depression. This has esthetic advantages and is also functionally of advantage since an inadvertent engaging under and remaining hanging at the proximal end of the outer sleeve is made difficult. The risk of the penetration of dirt is also reduced.

The inner component and the outer component can be movable toward each other between two end positions, wherein the proximal edge of the outer component is arranged at least in sections and in an encircling manner in the two end positions within the depression. In such a design, the proximal end is always arranged at least in sections in the depression irrespective of the relative position of the outer component and the inner component. It is particularly advantageous if the groove is sufficiently deep that the proximal end always remains in an encircling manner in the groove irrespective of the relative position of the outer component to the inner component.

One configuration makes provision for the inner component to have a first sleeve portion and for the outer component to have a second sleeve portion. An outer side of the first sleeve portion here has fixing means and/or guide means, by means of which the outer component is guided on and/or fastened to the inner component. An inner side of the first sleeve portion has a sealing surface, against which the second sleeve portion lies in a sealing manner such that a common interior of the two sleeve portions forms a portion of the applicator channel by means of which the discharge opening is connected to the plunger designed as a hollow tube.

The described design with a first sleeve portion as part of the inner component is of advantage since said sleeve portion fulfills a dual function. By means of structures on the outer side of the sleeve portion, the latter interacts with the outer component to the effect that the outer component is latched here or is limited in movement by means of stops. An outer thread for interaction with an inner thread on the outer component can also be provided on the outer side of the first sleeve portion. The second function resides in the inner-side sealing surface which, together with the second sleeve portion of the outer component, provides sealing of the applicator channel to the outside, such as in the manner of a telescopic channel portion.

In particular, it is of advantage if the inner component comprises a sleeve portion for the purpose of sealing in relation to the outer component and/or for the purpose of coupling the outer component to the inner component, and a central pin, the distal end of which interacts with the discharge opening for influencing the discharge, wherein a channel formed by the hollow tube leads into an intermediate space between the central pin and the sleeve portion.

In such a design, the inner component is therefore divided into two, as it were. The encircling sleeve portion interacts in a sealing manner with the outer component. The central pin can serve in particular to form the vortex chamber or can interact in some other way with the outer component, in particular with the end side thereof having the discharge opening, and therefore the guidance of the liquid and/or the discharge of the liquid can thereby be influenced or else occasionally suppressed.

A configuration according to the invention is distinguished by a fairly simple design. In particular, it is of advantage if the actuating surface and the base and the coupling device, provided on the latter, of the discharge head are designed as an integral component. The actuating surface and the plunger designed as a hollow tube likewise can be designed as an integral component.

By means of a combined configuration thereof, a discharge head can be obtained which consists of only two components, namely a first component comprising the base, the actuating handle with the actuating surface and the inner component of the nasal applicator, wherein at least the actuating handle is shiftable in relation to the base by deformability of the material, and a second component which forms the outer component of the nasal applicator. A highly cost-effective construction is therefore possible.

The outer component and the actuating surface can have different colorings and/or different materials. The two-colored design of the base and the outer component can be used in particular for the purpose of esthetic improvement, but also in order to adapt the discharge head to a company-specific typical coloring. Furthermore, the use of different materials makes it possible to select respectively ideally adapted materials for the outer component and the base together with the actuating handle. The outer component could thus be manufactured, for example, from a material which, by means of coating or inherent material properties, prevents growth of bacteria or which is perceived as haptically pleasant when in contact with the skin of the user, while the main component with the base and actuating handle can be composed of another material.

The actuating surface can be attached pivotably to the base, for example by a plastics bridge which connects the base and the actuating surface integrally and acts as a pivoting joint. It is furthermore particularly of advantage if, in the delivery state, a securing bridge is provided on a side of the actuating surface opposite the plastics bridge, said securing bridge connecting the actuating surface and the base integrally and intentionally breaking upon first actuation. Said integral design with a deformable plastics bridge as a joint is of advantage in the sense of a design consisting of few individual parts. The actuating surface is cut free in relation to the base on the far side of the plastics bridge by means of a slot, and therefore said actuating surface is movable. The effect achieved by the securing bridge is that an inadvertent discharge of liquid does not occur prior to commissioning since the commissioning requires a stronger application of force for the purpose of breaking said securing bridge.

An axis defined by the discharge direction of the discharge opening and/or by the center axis of rotation of the outer component in relation to the inner component can enclose an angle α of between 5° and 85°, for example an angle of between 10° and 50°, with a placing-on direction of the discharge head onto a pressure reservoir.

Said angling is customary in discharge heads of the type in question. It permits an advantageous use in which the pressure reservoir, the main direction of extent of which can coincide with the placing-on direction, can be held slightly angled and the nasal applicator can then be pushed at an appropriate angle into a nostril. In the case of a discharge head according to the invention, it is furthermore provided that the actuating surface and the nasal applicator are arranged next to each other, and therefore an asymmetrical shaping of the discharge head is provided.

The invention furthermore relates to a discharge head which can, but not absolutely, also have the features mentioned at the beginning and in particular the integral design of the inner component and the actuating surface, and which particularly is likewise provided for the nasal application of pharmaceutical liquids from a pressure reservoir which has an outlet valve with a valve connector, to which force can be applied counter to a spring force in order to open the outlet valve.

According to this aspect of the invention, said discharge head has an applicator, for example in the form of a nasal applicator, at the end of which a discharge opening is provided which is connected to an inlet of the applicator and therefore indirectly to the liquid reservoir through an applicator channel of the nasal applicator. Said applicator has an inner component and an outer component. The outer component is provided as a component which is separate from the inner component and is attached directly or indirectly to the inner component in such a manner that it is movable in a purely rotational manner in relation to the inner component.

The discharge opening is provided as an opening in the outer component and is surrounded on the inner side by an end-side inner surface. An end surface of the inner component is provided opposite the end-side inner surface, said end surface lying flat against the end-side inner surface.

At least two inflow channels in the form of inflow grooves are formed on the end-side inner surface of the outer component and/or on the end surface of the inner component, said inflow grooves being connected to an inflow region upstream of the inflow grooves, and therefore to the liquid reservoir, or being separated therefrom depending on a rotational position of the outer component with respect to the inner component.

Said inflow grooves therefore connect the inflow region, into which liquid first of all flows from the liquid reservoir, to the discharge opening. It is possible here by means of at least two inflow grooves of different design to influence the discharge characteristics of the liquid output through the discharge opening. If, in a first rotational position, the flow flows through a first of the inflow grooves while the second inflow groove is closed, the first inflow groove and the shape, orientation and throttling action thereof determines the discharge characteristics. If, for example, it is a radially oriented inflow groove, this does not lead to swirling and the liquid is discharged as a jet. If, in a second rotational position differing therefrom, the second inflow groove is opened instead of the first one, the shape, orientation and throttling action thereof determine the discharge characteristics. If, for example, it is a tangential groove which is oriented at an angle to the radial direction, the liquid can be imparted with a swirl which, during the discharge through the discharge opening, promotes the formation of a spray jet.

In principle, the opening and/or closing of the inflow grooves brought about by rotation of the outer component can also be used by itself in order to discharge different quantities of liquid, i.e. to obtain as it were an adjustable throttling effect. However, it is particularly of advantage if inflow grooves of two different types are provided, namely at least one substantially radially oriented radial groove and at least one tangential groove which is angled in relation thereto with respect to the discharge opening and the central direction of extent of which is not provided aligned with the discharge opening. The radial groove or the radial grooves serves or serve here for generating the already mentioned jet while the tangential groove or tangential grooves serves or serve for the formation of a vortex and therefore a spray jet. In each case a plurality of radial grooves and/or tangential grooves, for example in each case at least three, are provided which can be uniformly distributed over the circumference in order to bring about a uniform and substantially rotationally symmetrical discharge.

The at least two inflow grooves, i.e. in particular the at least one radial groove and the at least one tangential groove, are both provided in the region of the end-side inner surface of the outer component and the end surface of the inner component, wherein they can be arranged separated in such a manner that liquid cannot pass unintentionally from one inflow groove into the other inflow groove in each case and flow along said inflow groove to the discharge opening.

In order to be able to advantageously isolate the inflow grooves from each other, a design is of advantage in which at least one inflow groove is provided in the end-side inner surface of the outer component and at least one inflow groove is provided in the end surface of the inner component. Therefore, the two surfaces which are pressed against each other, the end-side inner surface of the outer component and the end side of the inner component, are used for the arrangement of the inflow grooves. By this means, the secure isolation thereof from each other is made possible even in the event of a small overall height. In particular, if radial and tangential grooves are provided and particularly if in each case a plurality of radial and tangential grooves are provided, the arrangement of the inflow grooves on the end-side inner surface and the end surface is of advantage.

The inner component and the outer component can lie tightly against each other not only in the region of the end-side inner surface and the end surface, but also in the region of a cylindrical inner surface adjacent to the end-side inner surface of the outer component and a cylindrical outer surface adjacent to the end surface of the inner component.

At least one of said two cylindrical surfaces is provided with a supply groove through which at least one inflow groove can be supplied with liquid from the inflow region. A plurality of such supply grooves which supply different inflow grooves with liquid depending on the rotational position can be provided in the surfaces.

As already discussed in respect of the end surface and the end-side inner surface with respect to the inflow grooves, in the region of the cylindrical inner surface and the cylindrical outer surface, supply grooves are provided both in the inner surface and in the outer surface. It has been shown that a particularly advantageous design is thus possible, by means of which the supply of liquid to the different inflow grooves can be permitted and interrupted. All of the flow paths from the inflow region to the discharge opening advantageously run in each case partially through a groove in the inner component and partially through a groove in the outer component.

A liquid path can be provided which, in the event of the corresponding rotational position of the outer component in relation to the inner component, runs through a supply groove provided in the cylindrical outer surface of the inner component, wherein said supply groove extends as far as the end surface of the inner component. Said liquid path can then run further into an inflow groove, which is provided on the end-side inner surface of the outer component, as far as the discharge opening. If, however, the outer component is rotated in relation thereto, said liquid path ends in the region of the end surface interrupted by the supply groove since the liquid path is blocked by the end-side inner surface of the outer component.

In a similar manner, a liquid path can run through a supply groove in the cylindrical inner surface of the outer component, but cannot extend here as far as the height of the end surface of the inner component. Instead, in a corresponding rotational position of the outer component in relation to the inner component, said liquid path can run further through an inflow groove which extends on the end surface of the inner component as far as the adjacent cylindrical outer surface.

The respective inflow grooves of the two liquid paths mentioned are arranged here in such a manner that, depending on the rotational position, only a portion of the inflow grooves are ever connected to their respective supply groove while another portion of the inflow grooves is separated from their respective supply groove. In the open state; the two liquid paths can run both through grooves in the inner component and also through grooves in the outer component.

In order to prevent the inadvertent exchange of liquid between the inflow grooves, i.e. in particular a liquid flow from a tangential groove into a radial groove or from a radial groove into a tangential groove, the end surfaces of the inner component and the end-side inner surface of the outer component lie in a sealing manner against one another. In order, despite the tolerances in the manufacturing process of the components, the inner component and the outer component, which can be formed as plastics parts, to prevent the end surface and the end-side inner surface from lifting off from each other, it is of advantage if the inner component and the outer component are provided with a spring device by means of which they are pressed against each other. A spring device is understood here as meaning an elastically deformed structure, the restoring force of which presses the end surface and the end-side inner surface against each other.

A design is particularly advantageous here in which the outer component and the inner component have inclined clamping surfaces which are pressed against each other by elastic deformation of the inner component or in particular of the outer component in a radial direction and thereby indirectly press the outer component and the inner component against each other. Use is made here of the fact that the outer component surrounds the inner component and can be elastically radially expanded by the latter. The corresponding restoring force is deflected in the region of the inclined clamping surfaces such that the end surface of the inner component and the end-side inner surface of the outer component are pressed against each other in the desired manner, and therefore liquid cannot flow from one inflow groove into another.

It is of particular advantage here if the inner component and/or the outer component have/has a shape of the clamping surfaces differing from the circular shape, and therefore, during a rotation of the outer component in relation to the inner component, at least one of the components undergoes a varying deformation which is minimal in particular in two end positions. This results in particular stability of the two end positions which can define two types of discharge—in particular in the form of a jet and in the form of a spray jet. Rotation from one such end position is associated with an increase in the deformation of one of the components, in particular the outer component, and therefore such a rotation can scarcely take place unintentionally. The invention furthermore also relates to a dispenser for discharging pharmaceutical liquids with a discharge head of the above-described types. This discharge head is fastened to a pressure reservoir of the dispenser, in which pharmaceutical liquid is stored under pressure and which, for its part, has an outlet valve. The outlet valve has a valve connector, to which force can be applied by means of the plunger of the discharge head counter to a spring force in order to open the valve.

The pressure reservoir can be bounded by a casing wall which is rotationally symmetrical with respect to the outer shape and is formed integrally or in a plurality of pieces with a domed base. The integrated valve can be integrated in a cover part which is connected to the casing surface by means of a crimp connection. The connecting region between casing surface and cover part can form a latching edge, in the region of which the discharge head is latched onto the pressure reservoir.

It is inherent to a pressure reservoir that the liquid stored therein is always under pressure, and therefore the pressure does not have to be generated for a discharging operation. Various possibilities are provided for exerting the pressure, for example the pressurization by propellant gas or by means of compressed air in the liquid reservoir or in particular in an intermediate region between a bag in the pressure reservoir and the casing wall of the pressure reservoir.

BRIEF DESCRIPTION OF THE DRAWINGS

Further advantages and aspects of the invention emerge from the claims and from the description below of preferred exemplary embodiments of the invention that are explained below with reference to the figures.

FIGS. 1A and 1B show a dispenser according to the invention in a sectioned and unsectioned overall illustration.

FIG. 2 shows the inner shaping of an outer sleeve of a nasal applicator of the discharge head of such a dispenser.

FIGS. 5A to 5I illustrate a third exemplary embodiment of the discharge head in detail.

DETAILED DESCRIPTION OF THE EXEMPLARY EMBODIMENTS

Figure 3:
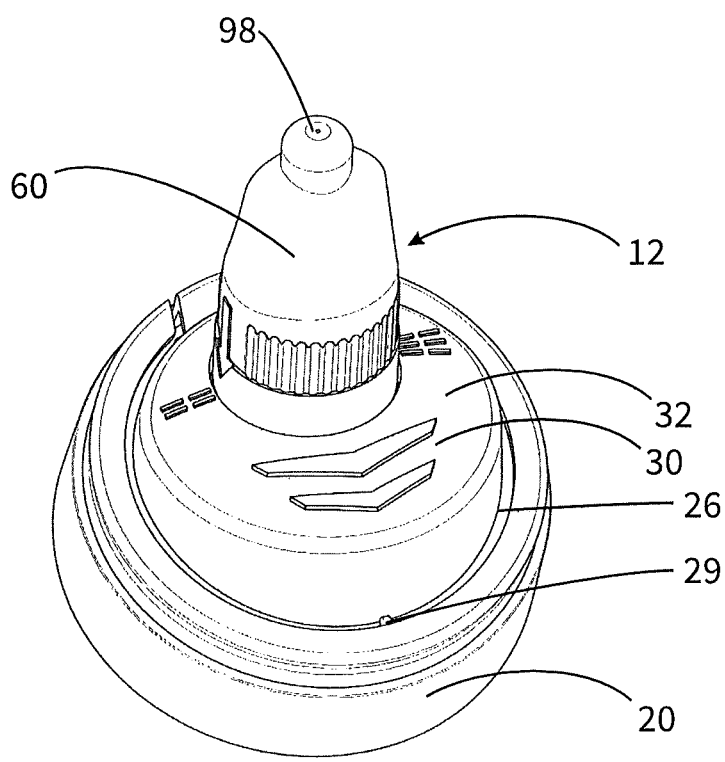
FIGS. 3 and 3A and 3B illustrate a first exemplary embodiment of the discharge head in detail.

FIGS. 1A and 1B show an overall illustration of a dispenser 100 according to the invention in a sectioned and unsectioned illustration. The relationships explained below in this regard apply here to various configurations of the discharge head 10 of this dispenser 100. Details regarding two possible configurations of the discharge head 10 will be explained subsequently with reference to FIGS. 3 and 4. A dispenser 100 according to the invention according to the present exemplary embodiments has a pressure reservoir 110, the outer surfaces of which are formed by a metal body 118 and a cover 120. An outlet valve 112 is fastened in the cover 120 and can be opened by pressing down a valve connector 114 counter to the force of a valve spring 116 such that the liquid flows into the discharge head 10.

The dispenser 100 according to the invention has a slender, elongate nasal applicator 12 on the discharge head 10, the main direction of extent of which nasal applicator is inclined in relation to the main direction of extent 3 of the pressure reservoir 110. The nasal applicator 12 is provided for pushing into a nostril of a user.

The discharge head 10 is snapped onto the pressure reservoir 110 in an installation direction 4 in the region of a crimp connection between the body 118 and the cover 120, wherein, for this purpose, a coupling device 22 with latching edges 24 is provided on a base 20 of the discharge head 10.

The base 20 of the discharge head 10 is connected integrally to most of the functional elements of the discharge head 10.

Thus, an actuating handle 30 with an actuating surface 32 is integrally formed on the base 20 via a plastics bridge 28. A plunger 40 designed as a hollow tube 42 is integrally formed on said actuating handle 30 and is pushed into the outlet valve 112 of the pressure reservoir 110 for the purpose of actuation and for the purpose of the inflow of liquid.

Furthermore, an inner component 50 of the nasal applicator 12 of the discharge head 10 is also formed integrally with the actuating handle 30. Said inner component 50 comprises an outer sleeve portion 56 and an inner pin 52.

The sole component of the discharge head 10 that is separated from said composite component is the outer component 60 of the nasal applicator 12, on the end side of which outer component an end wall is pierced by a discharge opening 98. The outer component 60 is pushed onto the inner component 50 and is fastened in a form-fitting manner to the inner component 50, as will also be explained further on.

The actuating handle 30 of the dispenser 100 is pivotable in the direction of the arrow 6 because of the deformability of the plastics bridge 28, and therefore the nasal applicator 12 and the plunger 40 are pivoted at the same time. By means of the pivoting of the plunger 40, the outlet valve 112 is opened and liquid flows upward through the inner channel 90 of the plunger 40, then passes into an intermediate space 58 between the central pin 52 and the sleeve portion 56 of the inner component 50 of the nasal applicator 12 and is conveyed from there through an applicator channel 92, which is jointly defined by the inner component 50 and the outer component 60, as far as the discharge opening 98 from where the liquid can be discharged. For the sealing of the components 50, 60 in relation to each other, the outer component has a sleeve 66, the outer side of which lies in a liquid-tight manner against the inside sealing surface of the sleeve 56.

A vortex chamber 96, the outer-component-side wall of which is illustrated in more detail in FIG. 2, is connected upstream of the discharge opening 98. The vortex chamber 96 is jointly bounded by the outer component 60 and the inner component 50, namely the end side of the central pin 52. It has inclined channels 96A through which liquid can flow in a swirled manner into the vortex chamber 96. Said swirl on exiting through the discharge opening 98 has the effect of forming a conical spray jet.

Figure 4:
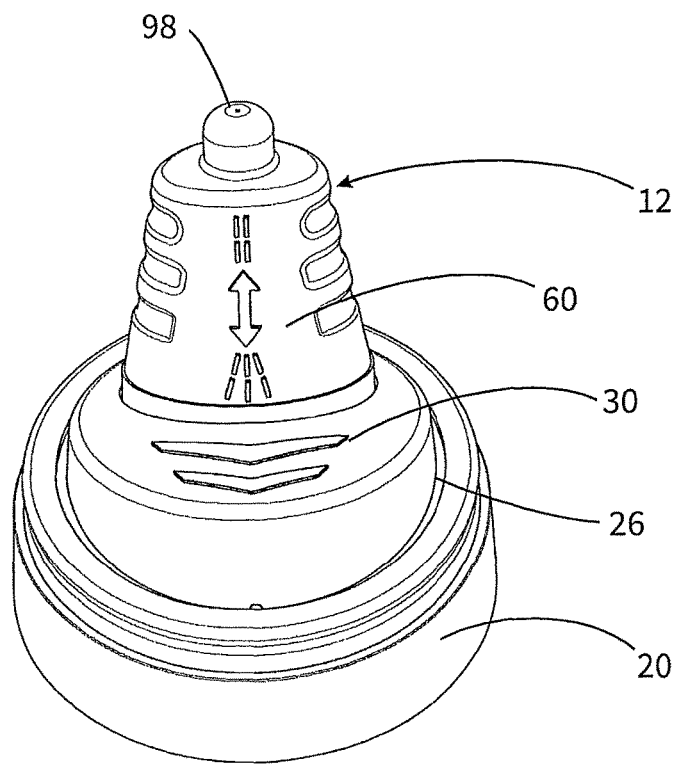
FIGS. 4 and 4A and 4B illustrate a second exemplary embodiment of the discharge head in detail.

In the design of FIGS. 1A and 1B and also in the two designs according to FIGS. 3 and 4, the outer component 60 is designed as an outer component 60 which is relatively movable to a limited extent.

This will be explained with respect to FIGS. 3 and 3A and 3B. This first configuration of a discharge head is shown in FIG. 3 in a perspective illustration. It is apparent therefrom that, although the base 20 and the actuating handle 30 with the actuating surface 32 are connected integrally to each other, they are sufficiently separated from each other by a gap 26 spanning approximately 300° in total, in order to permit relative movability after the breaking of a securing bridge 29.

In this design, the outer component 60 is formed in a combined rotational and linear manner in relation to the inner component 50 and the actuating handle 30. With regard to FIGS. 3A and 3B, this is achieved by a threaded connection being provided on the inner side 56B of a casing surface 68 of the outer component 60 and of an outer surface on the sleeve portion 56. A thread-like guide structure 56A is provided for this purpose on the outer side of the sleeve portion 56. By rotation of the outer component 60, shifting of the outer component 60 in relation to the inner component 50 can therefore be achieved with respect to the direction 2 illustrated in FIG. 3A.

By means of stops, not illustrated, the inner component 50 and the outer component 60 are designed to be rotated in relation to each other between two end positions spaced apart by 180° from each other, wherein this brings about an axial shifting of the outer component by a few millimeters.

Figure 3A:
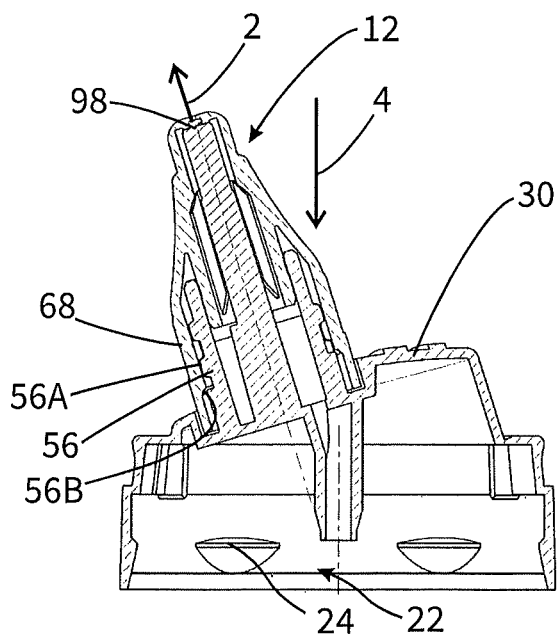

The first of the two end positions, which is illustrated in FIG. 3A, is designed to permit a spray jet, i.e. an atomization of the liquid during the discharge. Liquid which flows upon actuation into the applicator channel 92 has to flow in this relative position through the vortex channels 96A, which are apparent in FIG. 2, into the vortex chamber 96 such that the entire liquid flow is provided with a swirl and emerges as a conical spray jet.

Figure 3B:
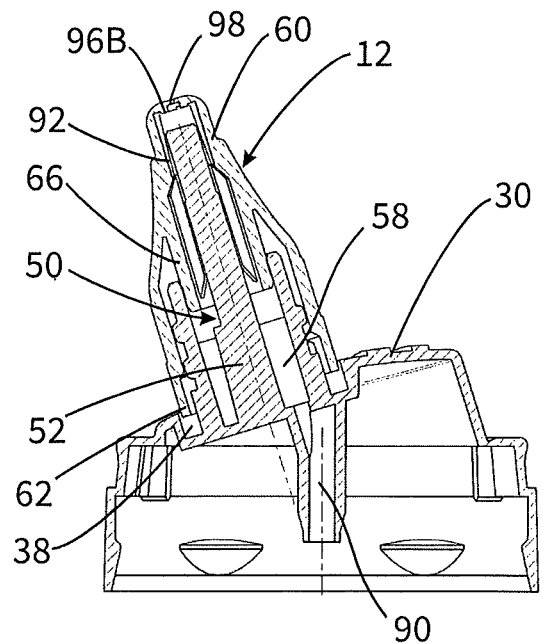

In the second end position of FIG. 3B, the discharge opening 98 like the web 96B having the vortex channels 96A is spaced apart from the distal end of the central pin 52 such that only a small portion of the liquid which flows in the direction of the discharge opening 98 is provided with a swirl. The discharge therefore takes place in the form of a substantially or completely unatomized jet.

By spacing the end positions apart by 180°, the effect is achieved that, despite a non-rotationally symmetrical shaping of the outer component 60, that can be seen from FIG. 3, the subjective feeling upon pushing the nasal applicator 12 into the nostril remains identical irrespective of the end position just achieved. This is achieved by the substantially flat-symmetrical outer form of the outer component 60.

As is apparent in particular with reference to FIGS. 3A and 3B, a groove-like depression 38 into which a proximal edge 62 of the outer component 60 projects is provided between the actuating surface 32 and the inner component 50. As is apparent with reference to the comparison of FIGS. 3A and 3B, the proximal edge 62 projects into the depression 38 to such an extent that it always remains within said depression 38 irrespective of the axial shifting of the outer component 60. Since only a small gap remains between the outer side of the outer component 60 and the outer flank of the depression 38, the penetration of dirt is unlikely here. In addition, an esthetically advantageous perception is obtained because the proximal edge 62 of the outer component generally cannot be seen by the end user.

Figure 4A:
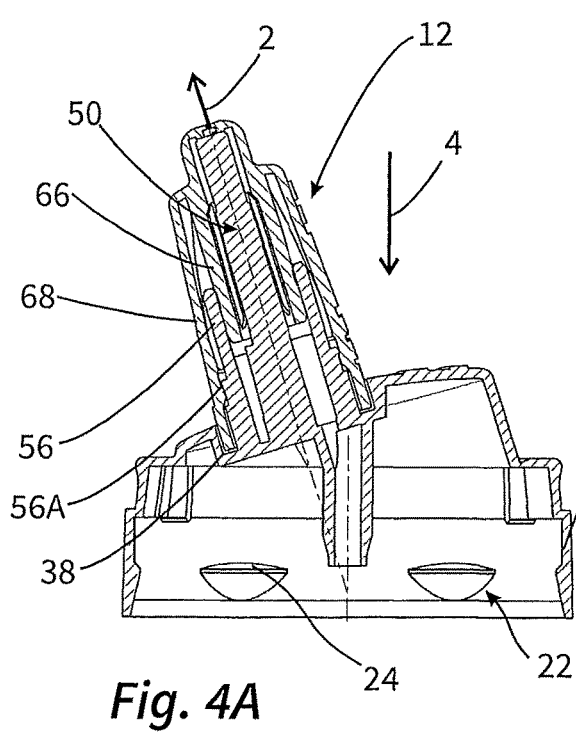
Figure 4B:
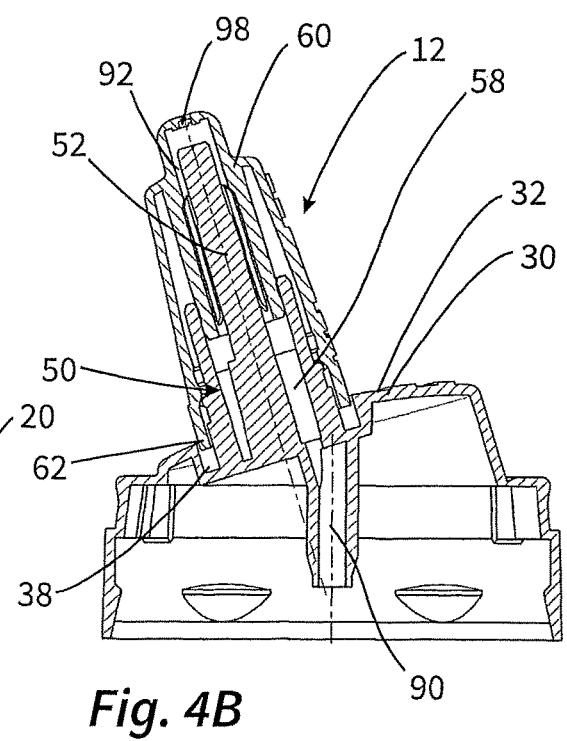

In the configuration according to FIGS. 4, 4A and 4B, the substantial difference over the preceding embodiment resides in the fact that no rotational relative shifting of the outer component 60 in relation to the inner component 50 is provided here. On the contrary, the outer component 60 has a rather elliptical shaping in cross section which, interacting with the groove-like depression 38, prevents a rotation.

Nevertheless, relative shiftability of the outer component 60 in relation to the inner component 50, namely purely linear movability, is in turn provided. The user can press the outer component 60 in the direction of the actuating handle 30 and can obtain the state of FIG. 4A here in which, in turn, similarly to the state of FIG. 3A, the liquid flowing out of the applicator channel 92 is forced to pass through the vortex channels 96A into the vortex chamber 96 and therefore to emerge in the form of a spray jet.

If, by contrast, the outer component 60 is shifted upward, i.e. away from the actuating handle 30, the state of FIG. 4B arises which, in turn, instead brings about the generation of a jet, i.e. an unatomized jet.

In the configuration of FIGS. 4A and 4B, the inner component 50 is designed very similarly to that of FIGS. 3A and 3B. However, the outer side of the sleeve 56 is provided with a latching structure which permits latching of the outer component 60 in the position of FIG. 4A. This prevents the outer component 60 from automatically and unintentionally merging as a result of the prevailing liquid pressure into the position of FIG. 4B.

FIGS. 5A to 5I show a further configuration of a discharge head according to the invention which is to be intentionally fastened in a manner corresponding to FIGS. 1A and 1B in order to form a dispenser 100 on a pressure reservoir 110.

In accordance with the preceding exemplary embodiments, said discharge head 10 has two components, namely—as can readily be seen in FIG. 5A—a first component which forms the base 20, the actuating handle 30 with actuating surface 32 and, integrally, an inner component 50 of the applicator, and a second component, namely an outer component 60, which is pushed onto the inner component 50 of the applicator and is latched here in the region of clamping surfaces 55, 65.

It is also provided in this exemplary embodiment that, according to FIGS. 5B and C, a switch can be made between different discharge characteristics, namely here between a discharge of the liquid in the form of a spray jet, on the one hand, and the discharge in the form of an unatomized jet, on the other hand. The switching over of the configurations takes place by the outer component 60 being rotated by 180° about the axis 2 in relation to the inner component 50. An axial shifting does not take place here.

In order, despite the absence of axial shifting, as in the configurations of FIGS. 3 and 4, to influence the characteristics of the discharge, a special shape of a distal interior 63 of the outer component 60 and of an end region 53 of the inner component 50 is provided. FIGS. 5D to 5G illustrate this.

Figure 5D:
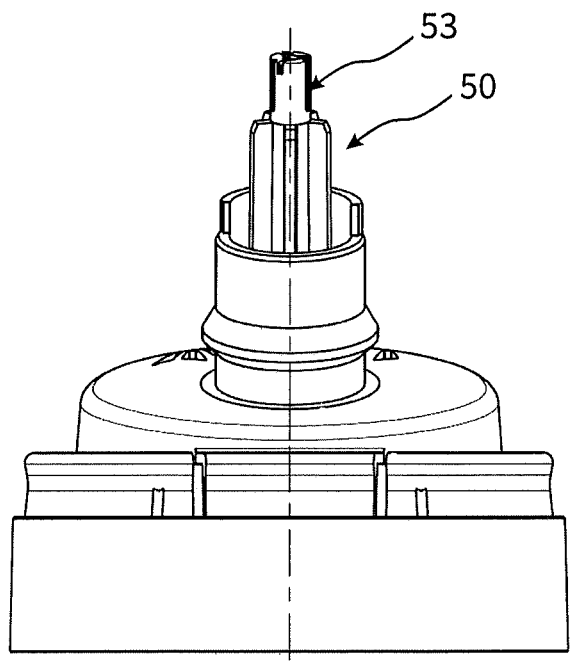
Figure 5E:
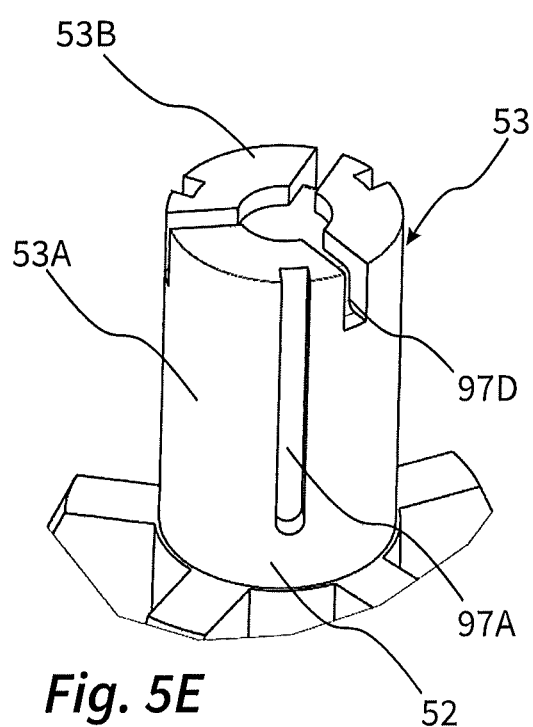
Figure 5F:
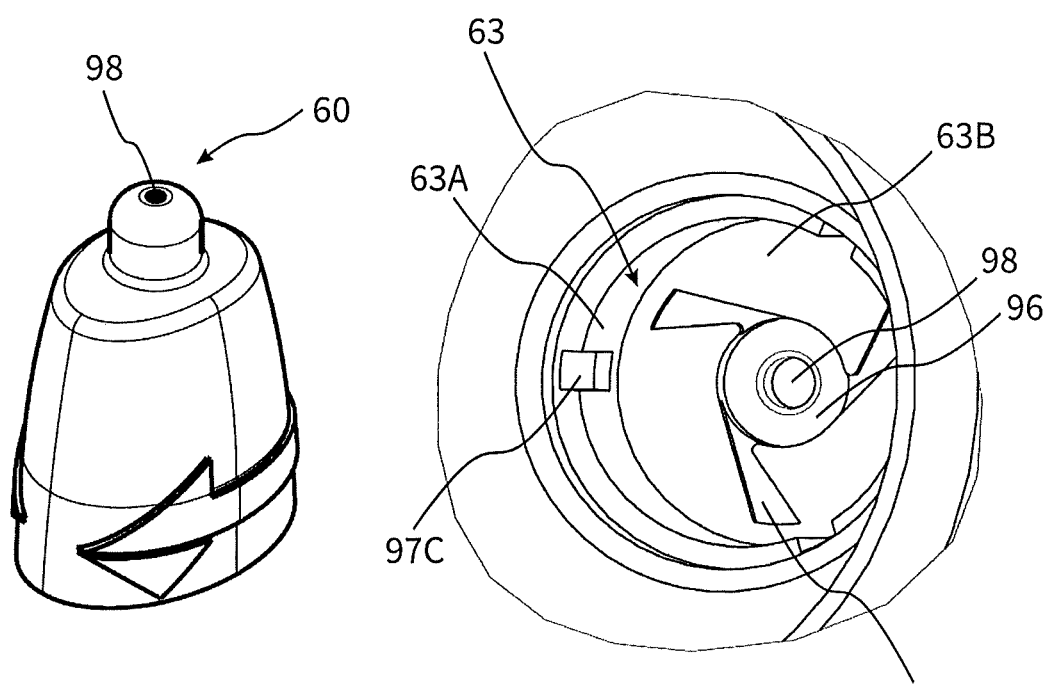
Figure 5G:
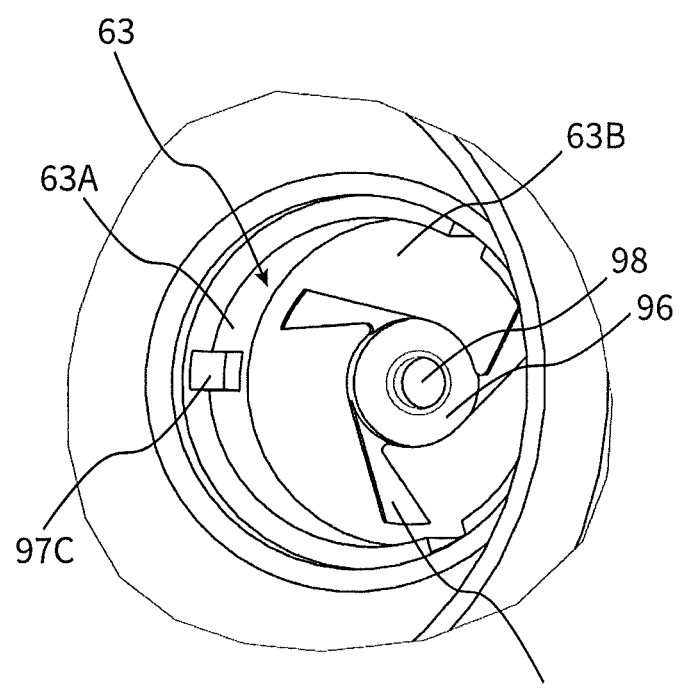

FIG. 5E shows the end region 53 of the inner component 50. Said end region has an initially circular-cylindrical basic shape, the dimensions of which, with respect to the diameter of an end surface 53B, correspond to the dimensions of the corresponding distal interior 63 of the outer component 60 such that the end region 53 is fitted into the distal interior 63 with encircling contact providing a seal on the end side.

It can be seen with regard to FIG. 5E that axially extending supply grooves 97A which extend as far as the end surface 53B are provided on an outside cylindrical surface 53A of the end region 53. A total of three supply grooves 97A at a distance of 120° from one another is involved. Offset by approximately 30° with respect thereto, three radial inflow grooves 97D are provided in the end surface 53B of the end region 53 of the inner component 50, said inflow grooves likewise each being spaced apart by 120° from one another and each extending as far as the cylindrical outer surface 53A.

Corresponding to this design with the grooves 97A, 97D in the end region 53 of the inner component 50, three grooves 97C which are offset by 120° in relation to one another are provided in an inside casing surface 63A on the outer component and do not extend as far as the end-side inner surface 63B, but rather find their respective end shortly before the latter. Three tangentially oriented inflow grooves 97B are provided in the end-side inner surface 63B itself, said inflow grooves leading tangentially into a vortex chamber 96 and are likewise spaced apart from one another by 120°.

This groove configuration is provided in order to open and to close various liquid paths depending on the rotational position of the outer component 60 in relation to the inner component 50.

This will be explained in more detail with reference also to FIGS. 5H and 5I.

Figure 5H:
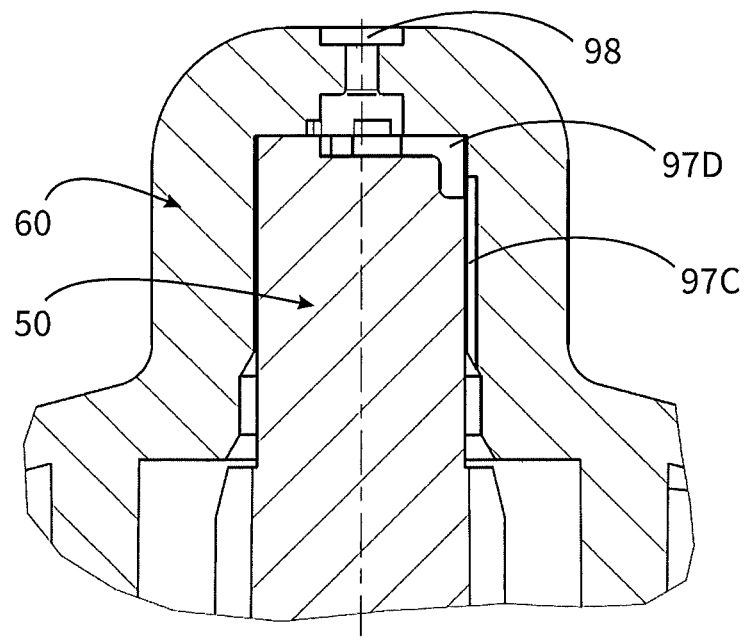

FIG. 5H shows that configuration in which the outer component 60 is rotated in relation to the inner component 50 in such a manner that an unatomized jet is intentionally intended to be discharged.

In this position, the supply grooves 97C are arranged in such a manner that liquid can flow at their end into the radial inflow grooves 97D and can thus pass as far as the discharge opening 98 without forming a swirl. At the same time, in this rotational position, the tangential grooves 97B are not supplied with liquid since they are arranged in a rotationally offset manner with respect to their supply grooves 97A.

Figure 5I:
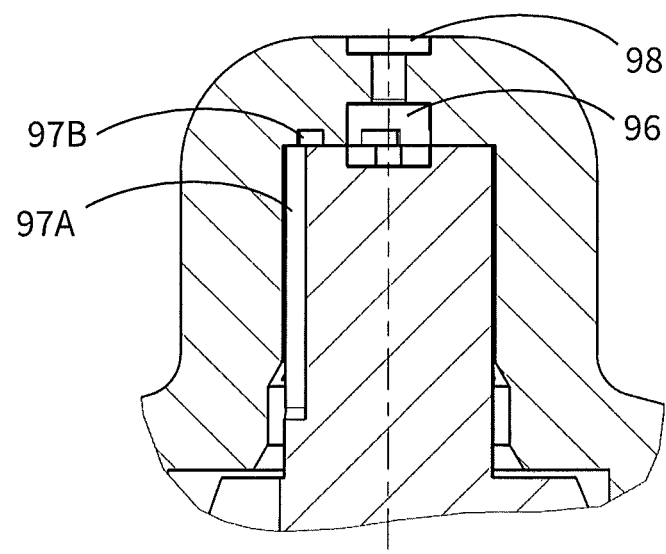

If the outer component 60 is now rotated by 180°, the situation of FIG. 5I arises. In this configuration, the supply grooves 97A are aligned with the inlets into the tangential grooves 97B. Liquid can thus pass into the tangential grooves 97B and can flow in the latter into the vortex chamber 96 with a swirl being formed and can be discharged as a spray jet through the discharge opening 98. The radial grooves 97D which would disturb the formation of the spray jet if liquid could likewise flow in here are without function in this rotational position since they are not in an aligned arrangement with their supply grooves 97C.

The described groove design therefore makes it possible to provide highly functionally reliable liquid paths which are sealed in relation to one another both for the formation of a spray jet and for the formation of a jet, wherein the paths can be opened and closed solely by means of a rotational movement of the outer component in relation to the inner component.

So that no liquid can enter the wrong inflow groove in the region between the end surface 53B and the end-side inner surface 63B, it is important that said surfaces lie as tightly against each other as possible. In particular the fact that sealing contact is also provided between the cylindrical surfaces 53A and 53B means that said sealing contact is made difficult in the end region. In order nevertheless to make it reliably possible, the already mentioned clamping surfaces 65, 55 which can be seen in FIG. 5A are provided. Said clamping surfaces are inclined approximately by 45° in relation to an axial direction 2. The outer component 60 is elastically expanded such that its restoring force forcibly applies the mutually opposite clamping surfaces 65 permanently against each other. Owing to the opposite clamping surfaces 55 of the inner component 50, the outer component is thereby permanently forcibly applied downward such that the end-side inner surface 63B is securely and flatly pressed against the end surface 53B.

The invention claimed is:

1. A discharge for the nasal application of pharmaceutical liquid from a pressure reservoir having an outlet valve with a valve connector, to which valve connector a force can be applied counter to a spring force in order to open the outlet valve, the discharge head comprising:
   a base and a coupling device provided on the base, the discharge head being fastenable to the pressure reservoir via the coupling device;
   an actuating surface disposed externally on the discharge head and shiftable in relation to the base, and a plunger configured as a hollow tube disposed on the base, said plunger being shiftable together with the actuating surface for the purpose of applying the force to the valve connector of the pressure reservoir; and
   a nasal applicator extending outward from the actuating surface and having an end with a discharge opening, said discharge opening being connected in a fluid-communicating manner to the hollow tube through an applicator channel of the nasal applicator, the nasal applicator having an inner component connected integrally to the actuating surface and an outer component separate from the inner component and attached to the inner component in a surrounding manner, the discharge opening being provided as an opening in the outer component, the outer component and the inner component together bounding the applicator channel, the outer component being attached to the inner component such that, in an attached state, the outer component is movable relative to the inner component, and the inner component and the outer component being configured such that the applicator channel is variable in cross-section by a relative shifting of the inner component and the outer component.

2. The discharge head as claimed in claim 1, wherein the inner component and the outer component together form a vortex chamber disposed upstream of the discharge opening.

3. The discharge head as claimed in claim 1, wherein the inner component and the outer component are configured such that characteristics of the liquid flowing out through the discharge opening are influenced by the relative movability of the inner component and the outer component at an identical inflow pressure of liquid into the nasal applicator.

4. The discharge head as claimed in claim 1, wherein the outer component is movable solely in a linear manner in relation to the inner component.

5. The discharge head as claimed in claim 1, further comprising a depression disposed in a transition region between the inner component and the actuating surface, and a proximal edge of the outer component dips into said depression in at least one end position of the outer component in relation to the inner component.

6. The discharge head as claimed in claim 5, wherein the inner component and the outer component are movable relative to each other between two end positions, the proximal edge of the outer component being arranged at least in sections in the two end positions within the depression.

7. The discharge head as claimed in claim 1, wherein the actuating surface, the base and the coupling device of the discharge head are configured as an integral one-piece component.

8. The discharge head as claimed in claim 1, wherein the outer component and the actuating surface have different colorings or are constructed of different materials.

9. The discharge head as claimed in claim 1, wherein the actuating surface is attached pivotably to the base.

10. The discharge head as claimed in claim 1, comprising one of the following:
    an axis defined by a discharge direction of the discharge opening, or a center axis of rotation of the outer component in relation to the inner component, encloses an angle of between 5° and 85° with a placing-on direction of the discharge head onto a pressure reservoir; or
    the nasal applicator is configured as an elongate applicator with a length of at least 20 mm protruding from the actuating surface; or
    the nasal applicator is configured as an elongate applicator with a shape tapering in a direction of the discharge opening; or
    the discharge opening has a minimum cross-sectional area of less than 4 mm$^2$; or
    a vortex chamber formed by the inner component and the outer component, the vortex chamber including at least one surface for generating a swirl, said surface being inclined in relation to a direction tangential to a discharge direction, said surface being provided on an inner side of the outer component; or
    the coupling device comprises latching edges integrally formed on the base and latchable on a coupling edge of the pressure reservoir; or
    the inner component comprises a sleeve portion for the purpose of sealing in relation to the outer component or for the purpose of coupling the outer component to the inner component, and a central pin, a distal end of the central pin interacting with the discharge opening to influence discharge of liquid therefrom, wherein a channel formed by the hollow tube leads into an intermediate space between the central pin and the sleeve portion; or
    the outer component is prevented by stop surfaces from separating from the inner component, wherein said stop surfaces are arranged and configured such that, via an increased application of force, the stop surfaces permit separation of the outer component from the inner component without destruction such that the outer component is exchangeable for another outer component.

11. The discharge head as claimed in claim wherein the outer component is movable in a combined linear and rotational manner in relation to the inner component, or the outer component is movable solely in a rotational manner in relation to the inner component.

12. The discharge head as claimed in claim 1, wherein the actuating surface and the plunger are configured as an integral one-piece component.

13. The discharge head as claimed in claim 1, wherein the actuating surface and inner component comprise an integral one-piece component.

14. The discharge head as claimed in claim 1, wherein the inner component and the outer component together define an annular part of the applicator channel.

15. A discharge head for the nasal application of pharmaceutical liquid from a pressure reservoir having an outlet valve with a valve connector, to which valve connector a force can be applied counter to a spring force in order to open the outlet valve, the discharge head comprising:
    a base and a coupling device provided on the base, the discharge head being fastenable to the pressure reservoir via the coupling device;
    an actuating surface disposed externally on the discharge head and shiftable in relation to the base, and a plunger configured as a hollow tube disposed on the base, said plunger being shiftable together with the actuating surface for the purpose of applying the force to the valve connector of the pressure reservoir; and
    a nasal applicator extending outward from the actuating surface and having an end with a discharge opening, said discharge opening being connected in a fluid-communicating manner to the hollow tube through an applicator channel of the nasal applicator, the nasal applicator having an inner component connected integrally to the actuating surface and an outer component separate from the inner component and attached to the inner component in a surrounding manner, the discharge opening being provided as an opening in the outer component, the outer component and the inner component together bounding the applicator channel, the inner component having a first sleeve portion, the outer component having a second sleeve portion, an outer side of the first sleeve portion having fixing means or guide means fastening the outer component to, or guiding the outer component on, the inner component, and an inner side of the first sleeve portion has a sealing surface, the second sleeve portion lying against the sealing surface in a sealing manner such that a common interior of the first and second sleeve portions forms a portion of the applicator channel, the discharge opening being fluidly connected to the plunger by the portion of the applicator channel.

16. The discharge head as claimed in claim 15, wherein the actuating surface and the plunger are configured as an integral one-piece component and the actuating surface is attached pivotably to the base.

17. A dispenser for discharging pharmaceutical liquids, comprising:
    a pressure reservoir storing pharmaceutical liquid under pressure, the pressure reservoir having an outlet valve, the outlet valve having a valve connector;
    a discharge head for coupling to the pressure reservoir, the discharge head comprising:

a base and a coupling device provided on the base, the discharge head being fastenable to the pressure reservoir via the coupling device;

an actuating surface disposed externally on the discharge head and shiftable in relation to the base and a plunger configured as a hollow tube disposed on the base, the plunger being shiftable together with the actuating surface to apply a force counter to a spring force to the valve connector of the pressure reservoir to open the outlet valve; and a nasal applicator extending outward from the actuating surface and having an end with a discharge opening, the discharge opening being connected in a fluid-communicating manner to the hollow tube through an applicator channel of the nasal applicator, the nasal applicator having an inner component connected integrally to the actuating surface, an outer component separate from the inner component and attached to the inner component in a surrounding manner, the discharge opening being provided as an opening in the outer component, the outer component and the inner component together bounding the applicator channel, the outer component being attached to the inner component such that, in an attached state, the outer component is movable relative to the inner component, and the inner component and the outer component being configured such that the applicator channel is variable in cross-section by a relative shifting of the inner component and the outer component.

18. A discharge head for the nasal application of pharmaceutical liquid from a pressure reservoir having an outlet valve with a valve connector, to which valve connector a force can be applied counter to a spring force in order to open the outlet valve, the discharge head comprising:

a base and a coupling device provided on the base, the discharge head being fastenable to the pressure reservoir via the coupling device;

an actuating surface disposed externally on the discharge head and shiftable in relation to the base, and a plunger configured as a hollow tube disposed on the base, said plunger being shiftable together with the actuating surface for the purpose of applying the force to the valve connector of the pressure reservoir; and a nasal applicator extending outward from the actuating surface and having an end with a discharge opening, said discharge opening being connected in a fluid-communicating manner to the hollow tube through an applicator channel of the nasal applicator, the nasal applicator having an inner component connected integrally to the actuating surface and an outer component separate from the inner component and attached to the inner component in a surrounding manner, the discharge opening being provided as an opening in the outer component, the outer component and the inner component together bounding the applicator channel, the outer component being attached to the inner component such that, in an attached state, the outer component is movable solely in a rotational manner in relation to the inner component, and the inner component and the outer component are configured such that the applicator channel is variable geometrically by a relative shifting of the inner component and the outer component.

19. The discharge head as claimed in claim 18, further including a spring device pressing the inner component and the outer component against each other.

20. The discharge head as claimed in claim 19, wherein the outer component and the inner component have inclined clamping surfaces pressed against each other by elastic deformation of the inner component or of the outer component in a radial direction, and elastic deformation of the inner component or of the outer component forms the spring device and presses the outer component and the inner component against each other.

21. The discharge head as claimed in claim 20, wherein the clamping surface of the inner component or the outer component is shaped different from a circular shape such that during a rotation of the outer component in relation to the inner component, at least one of the inner or outer components undergoes a varying deformation.

22. The discharge head as claimed in claim 18, wherein the actuating surface and the plunger are configured as an integral one-piece component and the actuating surface is attached pivotably to the base.

* * * * *